United States Patent [19]

Kaufman

[11] 4,300,942
[45] Nov. 17, 1981

[54] N-(SUBSTITUTED CARBONYL) DERIVATIVES OF N-PHOS-PHINYLMETHYLGLYCINATES AND THE HERBICIDAL USE THEREOF

[75] Inventor: Robert J. Kaufman, University City, Mo.

[73] Assignee: Monsanto Company, St. Louis, Mo.

[21] Appl. No.: 162,706

[22] Filed: Jun. 25, 1980

Related U.S. Application Data

[62] Division of Ser. No. 947,134, Sep. 29, 1978, Pat. No. 4,251,258.

[51] Int. Cl.³ .................... A01N 57/12; C07F 9/40
[52] U.S. Cl. .................................. 71/87; 260/941; 260/502.5; 560/12
[58] Field of Search .................. 71/87, 86; 260/941, 260/502.5

[56] References Cited

U.S. PATENT DOCUMENTS

| | | | |
|---|---|---|---|
| 3,455,675 | 7/1969 | Irani | 71/86 |
| 3,799,758 | 3/1974 | Franz | 71/86 |
| 3,835,000 | 9/1974 | Franz et al. | 204/78 |
| 3,853,530 | 10/1974 | Franz | 71/86 |
| 3,933,946 | 1/1976 | Gaertner | 71/86 |
| 3,991,095 | 11/1976 | Gaertner | 71/86 |
| 4,035,177 | 7/1977 | Gaertner | 71/87 |
| 4,053,505 | 10/1977 | Dutra | 260/502.5 |
| 4,075,332 | 2/1978 | Oswald et al. | 71/87 |
| 4,173,463 | 11/1979 | Peterson et al. | 71/87 |

FOREIGN PATENT DOCUMENTS 849907 12/1976 Belgium .

Primary Examiner—Catherine L. Mills
Attorney, Agent, or Firm—Gordon F. Sieckmann; Donald W. Peterson

[57] ABSTRACT

This disclosure relates to N-(substituted carbonyl) tri-ester derivatives of N-phosphinylmethylglycine wherein a substituted thiocarbonyl, RS(CO)—, a substituted sulfinylcarbonyl,

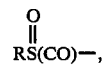

or a substituted sulfonyl carbonyl,

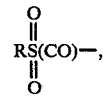

group is bonded to the nitrogen atom, to herbicidal compositions containing the same and to the herbicidal use thereof.

12 Claims, No Drawings

N-(SUBSTITUTED CARBONYL) DERIVATIVES OF N-PHOS-PHINYLMETHYLGLYCINATES AND THE HERBICIDAL USE THEREOF

This is a division of application Ser. No. 947,134, filed Sept. 29, 1978, now U.S. Pat. No. 4,251,258.

This invention relates to novel N-(substituted carbonyl)triester derivatives of N-phosphinylmethylglycine, to herbicidal compositions containing the same and to the herbicidal use thereof. More particularly, this invention is concerned with N-substituted triester derivatives of N-phosphinylmethylglycine wherein a substituted thiocarbonyl, RS(CO)—, a substituted sulfinylcarbonyl,

or a substituted sulfonylcarbonyl group,

is bonded to the nitrogen atom.

In accordance with U.S. Pat. No. 4,035,177, N-thiocarbonyl derivatives of N-phosphonomethylglycine having the formula

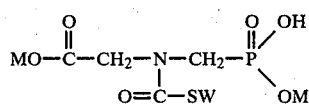

wherein M represents hydrogen, alkali metal, ammonium or lower alkyl ammonium and W is lower alkyl, phenyl or benzyl and phenyl or benzyl containing a chlorine, nitro, methyl, methoxy or trifluoromethyl substituent; are known to be active post-emergent herbicides.

N-phosphonomethylglycine, its salts, amides, esters and other derivatives are disclosed in U.S. Pat. No. 3,799,758 and are shown to be post-emergent herbicides. Other derivatives of N-phosphonomethylglycine and the plant growth regulation use thereof are disclosed in U.S. Pat. No. 3,853,530. The production of triesters of N-phosphonomethylglycine is disclosed in U.S. Pat. Nos. 4,053,505 and 3,835,000 and in Belgian Pat. No. 849,907.

The compounds of the present invention have the formula

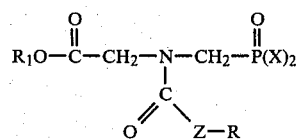

wherein R is selected from the group consisting of lower alkyl, lower alkenyl, lower alkynyl or benzyl; $R_1$ is selected from the group consisting of lower alkyl or lower alkoxyalkyl; Z is selected from the group consisting of thio, —S—, sulfinyl,

or sulfonyl,

and when Z is sulfinyl or sulfonyl,
X is $R_2$, wherein $R_2$ is phenoxy or phenoxy substituted with up to three groups individually selected from the class consisting of lower alkyl, lower alkoxy, halogen and nitro; and when Z is thio, X is $R_3$, wherein $R_3$ is a member of the group consisting of $R_2$, hydroxyl, chloro, morpholino, pyrrolidino, lower alkylamino, lower dialkylamino, lower alkenylamino, lower dialkenylamino, lower alkylthio, phenylthio, or substituted phenylthio where there is up to three substituents individually selected from the class consisting of lower alkyl, lower alkoxy, nitro and halogen.

As employed herein, the term "lower" designates those aliphatic hydrocarbon radicals which have up to 4 carbon atoms in a straight or branched chain. The term lower alkyl includes methyl, ethyl, propyl, isopropyl, butyl, isobutyl and the like. Lower alkenyl and lower alkynyl groups include vinyl, allyl, propenyl, butenyl, ethynyl, propargyl, butynyl and the like.

The term "halogen" as used herein includes chloro, bromo, fluoro and iodo.

Illustrative of the substituted phenxoy or phenylthio groups which $R_2$ and $R_3$ represent are monosubstituted phenoxy or phenylthio groups wherein the substituent is in the ortho, meta or para position, for example, methylphenoxy, butylphenoxy, methoxyphenoxy, butoxyphenoxy, fluorophenoxy, chlorophenoxy, bromophenoxy, iodophenoxy, nitrophenoxy, methylphenylthio, ethylphenylthio, propylphenylthio, butylphenylthio, methoxyphenylthio, butoxyphenylthio, fluorophenylthio, chlorophenylthio, bromophenylthio, iodophenylthio, nitrophenylthio and the like and the di- and tri-substituted phenoxy or phenylthio groups wherein the substituents are the same or different and are located in the 2, 3, 4, 5 or 6 positions of the phenyl ring, for example, dimethylphenoxy, dibutylphenoxy, (methyl) (butyl)phenoxy, dimethoxyphenoxy, dibutoxyphenoxy, (methoxy) (butoxy)phenoxy, difluorophenoxy, dichlorophenoxy, dibromophenoxy, fluorochlorophenoxy, butylfluorophenoxy, methylchlorophenoxy, methoxybromophenoxy, ethoxychlorophenoxy, methylnitrophenoxy, nitrochlorophenoxy, dinitrophenoxy, diethylphenylthio, dimethoxyphenylthio, dichlorophenylthio, fluorochlorophenylthio, methylchlorophenylthio, ethoxyfluorophenylthio, chloronitrophenylthio, trimethylphenoxy, (ethyl) (dimethyl)phenoxy, trichlorophenoxy, trimethoxyphenoxy, dimethylfluorophenoxy, trimethylphenylthio, (ethyl) (dimethyl)phenylthio, trichlorophenylthio, trimethoxyphenylthio, dimethylfluorophenylthio and the like.

In accordance with this invention, the N-(substituted carbonyl)-N-phosphinylmethylglycinate triester derivaties of formula (I) are produced in accordance with the following general procedure:

An aqueous solution containing an ester of N-phosphonomethylglycine having the formula

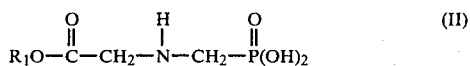

wherein $R_1$ is above defined; and sodium carbonate is reacted with carbonylsulfide followed by subsequent alkylation of the resulting sodium salt of N-thiocarbomate-N-phosphonomethylglycinate to produce the N-(substituted thiocarbonyl)-N-phosphonomethylglycinate having the formula

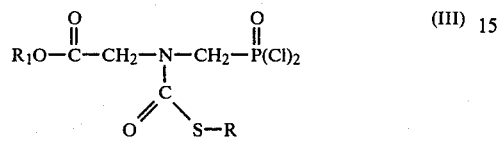

wherein R and $R_1$ are as above defined. This ester, (formula III) is treated with excess oxalyl chloride under anhydrous conditions and at a temperature range of 0°–50° C. to yield the N-(substituted thiocarbonyl)-N-[dichlorophosphinylmethyl]glycinate of formula (IV).

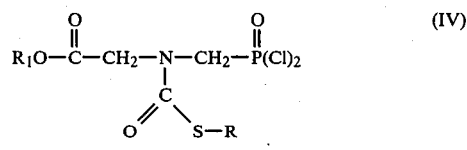

The dichloro derivative of formula (IV) is then reacted with a nucleophile

Y-H wherein Y is $R_2$, morpholino, pyrrolidino, lower alkylamino, lower dialkylamino, lower dialkenylamino, lower alkylthio, phenylthio or substituted phenylthio where there is up to three substituents individually selected from the class consisting of lower alkyl, lower alkoxy, nitro and halogen; in the presence of a tertiary amine hydrogen chloride acceptor to produce the novel N-(substituted thiocarbonyl) derivative having the formula

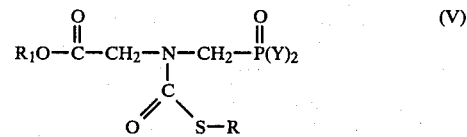

The process involving the reaction of the dichloro derivative of formula (IV) with the nucleophile can be conducted within a temperature range of 0°–50° C. with 25° C. being preferred. Although not narrowly critical, a reaction time from 2 to 48 hours is sufficient to complete the reaction. Aprotic solvents such as ether, benzene and the like, are preferred.

In preparing the N-(substituted thiocarbonyl) derivatives of formula (V), the ratio of reactants is not narrowly critical. For each mole of an N-(substituted thiocarbonyl)-N-phosphonomethylglycinate one must employ two moles of oxalyl chloride to produce one mole of the N-(substituted thiocarbonyl)-N-[dichlorophosphinylmethyl]glycinate. Also, one mole of the dichloro derivative reacts with two moles of the nucleophile, (Y-H). It is preferred to employ an excess of the oxalyl chloride and the nucleophile for ease of reaction and recovery of the reaction products.

In producing the N-(substituted thiocarbonyl) compounds of formula (V), the hydrogen chloride acceptor is preferably used in excess of stoichiometric to insure completeness of reaction. When the nucleophile (Y-H) being employed is a primary or secondary amine, an additional two moles of the nucleophile are used as the hydrogen chloride acceptor. In all other instances, the hydrogen chloride acceptor must be a tertiary amine, including tertiary alkylamines such as trimethylamine, triethylamine, tributylamine, trihexylamine and the like and aromatic tertiary amines such as pyridine, quinoline and the like.

When X is $R_2$, oxidation of the corresponding N-(substituted thiocarbonyl) derivative having the formula

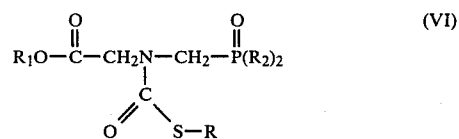

with metachloroperbenzoic acid in a suitable solvent yields the N-(substituted sulfinylcarbonyl) and the N-(substituted sulfonylcarbonyl) derivatives of formulas (VII) and (VIII) respectively.

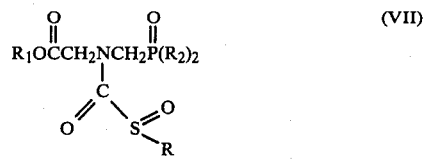

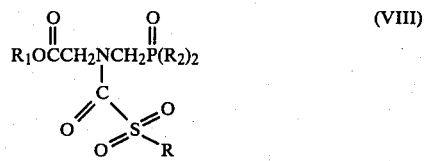

In the process for oxidizing the N-(substituted thiocarbonyl) derivative to produce the respective N-(substituted sulfinylcarbonyl) and N-(substituted sulfonylcarbonyl) derivatives, the ratio of reactants is extremely critical. A 1:1 molar ratio of metachloroperbenzoic acid and the N-(substituted thiocarbonyl) derivative of formula (VI) is essential if only the N-(substituted sulfinylcarbonyl) derivative of formula (VII) is to be prepared. If an excess of the N-(substituted thiocarbonyl) derivative is present, one obtains a mixture of compounds of formulas (V) and (VII) from which it is very difficult to separate the two components. An excess of metachlorobenzoic acid (greater than a 2.5:1 ratio) is required to exclusively produce the N-(substituted sulfonylcarbonyl) derivative of formula (VIII). If a ratio between 1:1 and 2.5:1 is used, one obtains a mixture of products from which it is very difficult to separate the compounds of formulas (VII) and (VIII).

When preparing the N-(substituted sulfinylcarbonyl) derivatives of formula (VII), the process can be conducted within a temperature range of −20° to 25° C. with 0° C. being preferred. It has been found that a reaction time of 1 to 3 hours is usually sufficient to complete the oxidation process.

In preparing the N-(substituted sulfonylcarbonyl) derivatives of formula (VIII) the process is conducted within a temperature range of 0°–50° C. with 25° C. being preferred. It has been found that a reaction time of 2 to 16 hours is usually sufficient to complete the oxidation process.

In the process for preparing the N-(substituted sulfinylcarbonyl) and the N-(substituted sulfonylcarbonyl) derivatives, solvents which are inert to the oxidizing medium and the reagents such as methylene chloride, chloroform, benzene, and the like are preferred.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

To ethyl-N-phosphonomethylglycinate (197 g.; 1.0 mol.) dissolved in 600 ml. of water at 0° C. was added sodium carbonate (159 g.; 1.5 mol). The resulting mixture was stirred until the gas evolution ceased. The resulting solution was added over a period of one hour to a solution of carbonyl sulfide (66 g.; 1.1 mol.) which previously had been condensed in 600 ml. of methanol at −20° C. in an ice-acetone bath. Following the addition, carbonyl sulfide was sparged through the reaction mixture for seven hours. To the mixture was added benzylchloride (171 g.; 1.0 mol.) and the resulting mixture was allowed to gradually warm to 25° C. over a period of 16 hours. The reaction mixture was then filtered and the methanol removed from the filtrate in vacuo. The residue was acidified to $pH_2$ by the addition of concentrated hydrochloric acid. An oil separated and was extracted into 2 liters of ethylacetate. The extract was dried over sodium sulfate and concentrated in vacuo to yield a viscous oil. The oil was dried over phosphorous pentoxide in a vacuum dessicator for 48 hours to yield ethyl-N-[(benzylthio)carbonyl]-N-(phosphonomethyl)-glycinate, monohydrate (250 g.) as a yellow glass having a melting point of 56°–58° C. and the following analysis:

CALCULATED: C, 42.74; H, 5.52; N, 3.83; P, 8.48; FOUND: C, 42.73; H, 5.45; N, 3.76; P, 8.61.

EXAMPLE 2

Ethyl-N-[(benzylthio)carbonyl]-N-(phosphonomethyl)-glycinate (15 g.; 0.043 mol.) was added to an excess of oxalyl chloride (50 ml.) at 25° C. The resulting solution was stirred for two hours at which point the gas evolution ceased. The solution was centrifuged to remove the precipitate and the supernatant liquid was concentrated in vacuo to yield ethyl-N-[(benzylthio)-carbonyl]-N-[dichlorophosphinylmethyl]-glycinate (10.5 g.) as an oil.

EXAMPLE 3

Freshly prepared ethyl-N-[(benzylthio)carbonyl]-N-[dichlorophosphinylmethyl]-glycinate (7.2 g.; 0.0189 mol.) dissolved in 50 ml. of diethyl ether was added to phenol (3.5 g.; 0.0375 mol.) and triethylamine (3.8 g.; 0.0375 mol.) in 50 ml of diethyl ether. The mixture was stirred for 16 hours at 25° C., then filtered and the filtrate was washed with water, dried over magnesium sulfate and concentrated in vacuo to yield an oily solid. The solid was triturated in diethyl ether and the ether layer was separated, washed with water, dried over magnesium sulfate and concentrated in vacuo. The residue was purified on a silica gel column using methylene chloride then diethyl ether as eluents to yield ethyl-N-[(benzylthio)carbonyl]-N-[bis(phenoxy)phosphinylmethyl]-glycinate (3.1 g.) as a solid having a melting point of 75°–77° C. and the following analysis: CALCULATED: C, 60.11; H, 5.25; N, 2.80; P, 6.20; S, 6.42; FOUND: C, 60.20; H, 5.30; N, 2.69; P, 5.97; S, 6.43.

EXAMPLE 4

Freshly prepared ethyl-N-[(benzylthio)carbonyl]-N-[dichlorophosphinylmethyl]-glycinate (6.1 g.; 0.016 mol.) dissolved in 50 ml. of diethyl ether was added to a solution containing dimethylamine (2.9 g.; 0.064 mol.) in 50 ml. of diethyl ether. The reaction mixture was stirred for 16 hours at 25° C., then filtered and the filtrate washed with water and 3% ammonium hydroxide. The ether layer was separated then dried and concentrated in vacuo. The residue was extracted with petroleum ether to yield ethyl-N-[(benzylthio)carbonyl]-N-[bis(dimethylamino)phosphinylmethyl]-glycinate as an oil ($n_D^{25}$=1.5355) having the following analysis:

CALCULATED: C, 50.86; H, 7.03; N, 10.47; P, 7.72; FOUND: C, 50.67; H, 6.89; N, 10.28; P, 7.67.

EXAMPLE 5

Freshly prepared ethyl-N-[(benzylthio)carbonyl]-N-[dichlorophosphinylmethyl]-glycinate (10.5 g.; 0.027 mol.) dissolved in 100 ml. of diethyl ether was added to a solution containing isopropylamine (6.7 g.; 0.11 mol.) in 50 ml. of diethyl ether. The reaction mixture was stirred for 2 hours at 25° C., then filtered. The filtrate was washed with 5% sodium bicarbonate, then water. The ether layer was separated, dried over sodium sulfate and concentrated in vacuo. To remove remaining traces of solvent, the residue was concentrated at 25° C. and 0.05 mm. and yielded ethyl-N-[(benzylthio)carbonyl]-N-[bis(isopropylamino)phosphinylmethyl]-glycinate (7.0 g.) as crystals having a melting point of 69°–72° C. and the following analysis:

CALCULATED: C, 53.13; H, 7.51; N, 9.78; FOUND: C, 53.03; H, 7.52; N, 9.74.

EXAMPLE 6

Freshly prepared ethyl-N-[(benzylthio)carbonyl]-N-[dichlorophosphinylmethyl]-glycinate (11.3 g.; 0.029 mol.) dissolved in 100 ml. of diethyl ether was added to a solution containing n-butylamine (8.6 g.; 0.118 mol.) in 100 ml. of diethyl ether. The reaction mixture was stirred for 16 hours at 25° C., then filtered. The filtrate was washed with water, dried over magnesium sulfate and concentrated in vacuo to yield ethyl-N-[(benzylthio)carbonyl]-N-[bis(n-butylamino)phosphinylmethyl]-glycinate (12.5 g.) as a solid having a melting point of 45°–48° C., and the following analysis:

CALCULATED: C, 55.12; H, 7.93; N, 9.18; FOUND: C, 55.44; H, 8.09; N, 8.72.

EXAMPLE 7

Freshly prepared ethyl-N-[(benzylthio)carbonyl]-N-[dichlorophosphinylmethyl]-glycinate (12 g.; 0.031 mol.) dissolved in 150 ml. of diethyl ether was added to a solution containing diallylamine (12.15 g.; 0.125 mol.) in 150 ml. of diethyl ether. The reaction mixture was stirred for 16 hours at 25° C., then filtered. The filtrate was washed with 3% ammonium hydroxide, 5% hydrochloric acid and then water. The ether layer was separated, then dried and concentrated in vacuo to yield ethyl-N-[(benzylthio)carbonyl]-N-[bis(diallylamino)-phosphinylmethyl]-glycinate, hemi-hydrate (10.1 g.) as an oil ($n_D^{25} = 1.5373$) having the following analysis:

CALCULATED: C, 58.30; H, 7.38; N, 8.16;
FOUND: C, 58.45; H, 7.27; N, 7.84.

EXAMPLE 8

Freshly prepared ethyl-N-[(benzylthio)carbonyl]-N-[dichlorophosphinylmethyl]-glycinate (12 g.; 0.031 mol.) dissolved in 200 ml. of diethyl ether was added to p-chlorophenol (7.8 g.; 0.061 mol.). To this mixture was added a solution of triethylamine (6.15 g.; 0.06 mol.) in 100 ml. of diethyl ether and the resulting mixture was stirred for 16 hours at 25° C. The reaction mixture was filtered, and the filtrate was washed with 5% sodium hydroxide, water, and 10% hydrochloric acid. The ether layer was separated and dried over magnesium sulfate and concentrated in vacuo to yield ethyl-N-[(benzylthio)carbonyl]-N-[bis(4-chlorophenoxy)phosphinylmethyl]-glycinate as an oil ($n_D^{25} = 1.5656$) having the following analysis:

CALCULATED: C, 52.83; H, 4.26; N, 2.46;
FOUND: C, 52.87; H, 4.28; N, 2.41.

EXAMPLE 9

A solution of triethylamine (7.25 g.; 0.072 mol.) in 100 ml. of diethyl ether was added dropwise to a solution of freshly prepared ethyl-N-[(benzylthio)carbonyl]-N-[dichlorophosphinylmethyl]-glycinate (13.8 g.; 0.036 mol.) and m-cresol (7.8 g.; 0.072 mol.) dissolved in 150 ml. of diethyl ether. The reaction mixture was stirred for 16 hours at 25° C., then filtered. The filtrate was washed with 5% sodium hydroxide, 10% hydrochloric acid, and brine. The ether layer was separated, dried over magnesium sulfate and concentrated in vacuo. The residue was taken up in methylene chloride and again washed, dried and concentrated to yield ethyl-N-[(benzylthio)carbonyl]-N-bis-(3-methylphenoxy)phosphinylmethyl]-glycinate as an oil ($n_D^{25} = 1.5589$) having the following analysis:

CALCULATED: C, 61.47; H, 5.73; N, 2.65;
FOUND: C, 61.62; H, 5.78; N, 2.64.

EXAMPLE 10

Freshly prepared ethyl-N-[(benzylthio)carbonyl]-N-[dichlorophosphinylmethyl]-glycinate (11.7 g.; 0.03 mol.) dissolved in 150 ml. diethyl ether was added to a p-methoxyphenol (7.6 g.; 0.06 mol.). To this mixture was added a solution of triethylamine (6.2 g.; 0.06 mol.) in 150 ml. of diethyl ether and the resulting mixture was stirred for 16 hours at 25° C. The reaction mixture was filtered and the filtrate washed twice with 5% sodium hydroxide, once with water, and with brine. The ether layer was separated, dried over magnesium sulfate and concentrated in vacuo. To remove any remaining traces of solvent, the residue was concentrated at 25° C. and 0.50 mm. and yielded ethyl-N-[(benzylthio)carbonyl]-N-[bis-(4-methoxyphenoxy) phosphinylmethyl]-glycinate (4.4 g.) as a solid having a melting point of 71°–75° C. and the following analysis:

CALCULATED: C, 57.95; H, 5.40; N, 2.50;
FOUND: C, 57.97; H, 5.41; N, 2.47.

EXAMPLE 11

A solution of freshly prepared ethyl-N-[(benzylthio)-carbonyl]-N-(dichlorophosphinylmethyl)-glycinate (13.1 g.; 0.034 mol.) and m-nitrophenol (9.3 g.; 0.067 mol.) dissolved in 200 ml. of diethyl ether was added to a solution of triethylamine (6.7 g.; 0.067 mol.) in 100 ml. of diethyl ether. The reaction mixture was stirred for 16 hours at 25° C., then filtered. The filtrate was washed with 5% sodium bicarbonate, water, and 10% hydrochloric acid. The ether layer was separated, dried over magnesium sulfate and concentrated in vacuo. The residue was dissolved in diethyl ether, then washed with 5% sodium bicarbonate, water, and 3% ammonium hydroxide. The ether layer was separated, dried over magnesium sulfate, and the residue was concentrated at 25° C. and 0.05 mm. for 16 hour to yield ethyl-N-[(benzylthio)carbonyl]-N-[bis(3-nitrophenoxy)phosphinylmethyl]-glycinate as an oil ($n_D^{25} = 1.5855$) having the following analysis:

CALCULATED: C, 50.94; H, 4.10; N, 7.13;
FOUND: C, 51.12; H, 4.12; N, 7.06.

EXAMPLE 12

Freshly prepared ethyl-N-[(benzylthio)carbonyl]-N-[dichlorophosphinylmethyl]-glycinate (12.55 g.; 0.033mol.) dissolved in 100 ml. of diethyl ether was added to a solution of pyrrolidine (9.3 g.; 0.13 mol.) in 100 ml. of diethyl ether. The reaction mixture was stirred for 16 hours at 25° C., then filtered. The filtrate was washed with water, dried with magnesium sulfate and concentrated in vacuo. To remove any remaining solvent, the residue was concentrated at 25° C. and 0.05 mm. to yield ethyl-N-[(benzylthio)carbonyl]-N-[bis(-pyrrolidyl)-phosphinylmethyl]-glycinate, hemi-hydrate as an oil ($n_D^{25} = 1.5424$) having the following analysis:

CALCULATED: C, 54.59; H, 7.09; N, 9.09;
FOUND: C, 54.95; H, 6.96; N, 8.74.

EXAMPLE 13

Freshly prepared ethyl-N-[(benzylthio)carbonyl]-N-[dichlorophosphinylmethyl]-glycinate (11.7 g.; 0.03 mol.) dissolved in 100 ml. of diethyl ether was added to a solution of isopropylthiol (4.6 g.; 0.061 mol.) in 50 ml. of diethyl ether. To this mixture was dropwise added a solution of triethylamine (6.2 g.; 0.061 mol.) in 100 ml. of diethyl ether. The resulting mixture was stirred for 16 hours at 25° C. The reaction mixture was filtered and the filtrate was washed with water and concentrated in vacuo. The residue was extracted with petroleum ether and the extract was concentrated at 25° C. and 0.05 mm. for six hours. The reaction was taken up in diethyl ether and washed with 3% ammonium hydroxide, 5% hydrochloric acid, and water. The ether layer was separated, dried with magnesium sulfate and concentrated in vacuo. To remove any remaining solvent, the residue was concentrated at 25° C. and 0.05 mm. for 16 hours and yielded ethyl-N-[(benzylthio)carbonyl]-N-[bis(isopropylthio)phosphinylmethyl]-glycinate as an oil ($n_D^{25} = 1.5578$) having the following analysis:

CALCULATED: C, 49.22; H, 6.52; N, 3.02;
FOUND: C, 49.05; H, 6.58; N, 3.00.

EXAMPLE 14

Freshly prepared ethyl-N-[(benzylthio)carbonyl]-N-[dichlorophosphinylmethyl]-glycinate (12.3 g.; 0.032 mol.) dissolved in 100 ml. of diethyl ether was added to p-chlorophenylthiol (8.8 g.; 0.061 mol.). To this solution was added a solution of triethylamine (6.1 g.; 0.061 mol.) in 100 ml. of diethyl ether and the mixture was stirred for 16 hours at 25° C. The reaction mixture was filtered and the filtrate was washed with water, dried with magnesium sulfate and concentrated in vacuo. The residue was purified using a silica gel column with methylene chloride and dietyl ether as the eluents to yield ethyl-N-[(benzylthio)carbonyl]-N-[bis-(4-chlorophenylthio)phosphinylmethyl]-glycinate (5.75 g.) as an oil ($n_D^{25} = 1.6228$) having the following analysis:

CALCULATED: C, 50.00; H, 4.03; N, 2.33; FOUND: C, 49.87; H, 4.08; N, 2.38.

EXAMPLE 15

Freshly prepared ethyl-N-[(benzylthio)carbonyl]-N-[dichlorophosphinylmethyl]-glycinate (10.4 g.; 0.03 mol.) dissolved in 100 ml. of diethyl ether was added to a solution of phenylthiol (6.6 g.; 0.06 mol.) and triethylamine (6.05 g.; 0.06 mol.) in diethyl ether (100 ml.). The reaction mixture was stirred for 16 hours at 25° C., then filtered and the filtrate washed with 5% sodium hydroxide, 5% hydrochloric acid, and brine. The ether layer was separated, dried over sodium sulfate and concentrated in vacuo. The crude material was purified on a silica gel column using first benzene then a 1:1 mixture of diethyl ether and benzene as eluents. To remove any remaining traces of solvent, the residue was concentrated at 25° C. and 0.05 mm. and yielded ethyl-N-[(benzylthio)carbonyl]-N-[bis-(phenylthio)phosphinylmethyl]-glycinate as an oil ($n_D^{25} = 1.6233$) having the following analysis:

CALCULATED: N, 2.63; P, 5.83; S, 18.09; FOUND: N, 2.70; P, 5.76; S, 17.93.

EXAMPLE 16

Freshly prepared ethyl-N-[(benzylthio)carbonyl]-N-[dichlorophosphinylmethyl]glycinate (11.6 g.; 0.033 mol.) dissolved in 75 ml. of diethyl ether and methanethiol (3.2 g.; 0.066 mol.) were added to a solution of triethylamine (6.75 g.; 0.066 mol.) in 75 ml. of diethyl ether. After stirring for four hours at 25° C., the reaction mixture was filtered and the filtrate washed with 5% sodium hydroxide, 5% hydrochloric acid, and brine. The ether layer was separated, dried and concentrated in vacuo. The residue was purified on a silica gel column using diethyl ether as the eluent. To remove any remaining traces of solvent, the residue was concentrated at 25° C. and 0.05 mm. and yielded ethyl-N-[(benzylthio)carbonyl]-N-[bis(methylthio)phosphinylmethyl]glycinate as an oil ($n_D^{25} = 1.5888$) having the following analysis:

CALCULATED: N, 3.44; P, 7.60; S, 23.60; FOUND: N, 3.64; P, 7.70; S, 23.84.

EXAMPLE 17

Freshly prepared ethyl-N-[(benzylthio)carbonyl]-N-[dichlorophosphinylmethyl]-glycinate (11.7 g.; 0.03 mol.) dissolved in 100 ml. of diethyl ether was added to m-methoxyphenylthiol (8.1 g.; 0.058 mol.). To this mixture was added a solution of triethylamine (5.8 g.; 0.058 mol.) in 100 ml. of diethyl ether and the resultant mixture was stirred for 16 hours at 25° C. The reaction mixture was filtered and the filtrate washed with water and concentrated in vacuo. The residue was purified on a silica gel column using methylene chloride then diethyl ether as the eluents to yield ethyl-N-[(benzylthio)carbonyl]-N-[bis(3-methoxyphenylthio)phosphinylmethyl]-glycinate as an oil ($n_D^{25} = 1.6064$) having the following analysis:

CALCULATED: C, 54.81; H, 5.11; N, 2.37; FOUND: C, 54.97; H, 5.15; N, 2.45.

EXAMPLE 18

Freshyl prepared ethyl-N-[(benzylthio)carbonyl]-N-[dichlorophosphinylmethyl]-glycinate (13.2 g.; 0.034 mol.) dissolved in 100 ml. of diethyl ether was added to m-chlorophenol (8.8 g.; 0.068 mol.) and triethylamine (6.9 g.; 0.068 mol.). The reaction mixture was stirred for 16 hours at 25° C., then filtered. The filtrate was washed with 5% sodium hydroxide, 10% hydrochloric acid, dried, and concentrated in vacuo. The residue was purified on a silica gel column using methylene chloride as the eluent. To remove any remaining traces of solvent, the residue was concentrated at 25° C. and 0.05 mm. and yielded ethyl-N-[(benzylthio)carbonyl]-N-[bis-(3-chlorophenoxy)phosphinylmethyl]-glycinate as an oil ($n_D^{25} = 1.5632$) having the following analysis:

CALCULATED: C, 52.83; H, 4.26; N, 2.46; FOUND: C, 53.04; H, 4.31; N, 2.54.

EXAMPLE 19 n-Butyl-N-(phosphonomethyl)-glycinate (13.2 g.; 0.0587 mol.) was added to a solution of sodium carbonate (9.3 g.; 0.088 mol.) in 100 ml. of water. After the ester completely dissolved, thioallylchloroformate (12.0 g.; 0.088 mol.) was added to the solution. The resulting mixture was stirred for 4 hours, then extracted with two 100 ml. portions of diethyl ether. The aqueous layer was separated and acidified to pH2 with concentrated hydrochloric acid. The resultant oily precipitate was extracted with ethyl acetate and the extract dried over sodium sulfate and concentrated in vacuo to yield n-butyl-N-[(allylthio)carbonyl]-N-(phosphonomethyl)-glycinate (20 g.). A portion of the n-butyl-N-[(allylthio)carbonyl]-N-(phosphonomethyl)-glycinate (17.5 g.) was dissolved in an excess of oxalyl chloride (50 ml.). After gas evolution had ceased, the solution was concentrated in vacuo to yield n-butyl-N-[(allylthio)carbonyl]-N-[dichlorophosphinylmethyl]-glycinate (10.5 g.; 0.028 mol.) which was used without further purification. The dichloro derivative was dissolved in 100 ml. of diethyl ether and added to m-chlorophenol (7.2 g.; 0.056 mol.). To the mixture was added a solution of triethylamine (5.6 g.; 0.056 mol.) in 50 ml. of diethyl ether. The reaction mixture was stirred for 16 hours at 25° C. and filtered. The filtrate was washed with 5% sodium hydroxide, brine, 5% hydrochloric acid and again with brine. The ether layer was separated, dried over sodium sulfate and concentrated in vacuo. The residue was purified on a silica gel column using methylene chloride as the eluent to yield n-butyl-N-[(allylthio)carbonyl]-N-[bis(3-chlorophenoxy)phosphinylmethyl]-glycinate (2.6 g.) as an oil ($n_D^{25} = 1.5560$) having the following analysis:

CALCULATED: C, 50.56; H, 4.80; N, 2.56; FOUND: C, 50.19; H, 4.74; N, 2.44.

EXAMPLE 20 n-Butyl-N-[(allylthio)carbonyl]-N-(dichlorophosphinylmethyl)-glycinate (9.5 g.; 0.026 mol.) dissolved in 100 ml. of diethyl ether was added to isopropylthiol (3.5 g.; 0.052 mol.). To this mixture was added a solution of triethylamine (5.3 g.; 0.053 mol.) in 50 ml. of diethyl ether. The reaction mixture was stirred for 16 hours at 25° C. and filtered. The filtrate was washed with 3% ammonium hydroxide, brine, 5% hydrochloric acid, and again with brine. The ether layer was separated, dried and concentrated in vacuo to yield n-butyl-N-[(allylthio)carbonyl]-N-[bis(isopropylthio)phosphinylmethyl]-glycinate as an oil ($n_D^{25} = 1.5289$) having the following analysis:
CALCULATED: C, 46.24; H, 7.30; N, 3.17;
FOUND: C, 45.55; H, 7.33; N, 3.09.

EXAMPLE 21

(2-Ethoxy)ethyl-N-(phosphonomethyl)-glycinate (24.1 g.; 0.1 mol.) was dissolved in a solution of sodium carbonate (15.9 g.; 0.15 mol.) in 200 ml. of water. To the resulting solution was added 200 ml. of methanol and carbonyl sulfide was then sparged through the reaction mixture for 7.25 hours. To the mixture was added propargyl bromide (13.1 g.; 0.11 mol.) and the mixture was stirred for 16 hours at 25° C. The solution was extracted twice with diethyl ether and the aqueous layer was then acidified to pH2 with concentrated hydrochloric acid. The resultant oily precipitate was extracted twice with 500 ml. of ethyl acetate and the extract dried over sodium sulfate and concentrated in vacuo. To remove any remaining traces of solvent, the residue was concentrated at 25° C. and 0.05 mm. and yielded (2-ethoxy)-ethyl-N-[(propargylthio)carbonyl]-N-(phosphonomethyl)glycinate (26 g.). This compound was treated with an excess of oxalyl chloride (50 ml.) and stirred for one hour. The solution was concentrated in vacuo to yield (2-ethoxy)ethyl-N-[(propargylthio)carbonyl]-N-[dichlorophosphinylmethyl]glycinate (23.1 g.; 0.064 mol.).

A portion of this material (12.65 g.; 0.034 mol.) and 2-chloro-4-fluorophenol (9.85 g.; 0.061 mol.) were dissolved in 50 ml. of diethyl ether and 50 ml. of methylene chloride. To this mixture was added solution of triethylamine (6.8 g.; 0.068 mol.) in 100 ml. of diethyl ether. The resulting mixture was stirred for 16 hours at 25° C. and filtered. The filtrate was washed with 5% sodium hydroxide, brine, 5% hydrochloric acid and again with brine. The ether layer was separated, dried and concentrated in vacuo. A portion of the residue (8.5 g.) was purified on a silica gel column using chloroform as the eluent to yield (2-ethoxy)ethyl N-[(propargylthio)carbonyl]-N-[bis(2'-chloro-4'-fluorophenoxy)phosphinylmethyl]glycinate as an oil ($n_D^{25} = 1.5289$) having the following analysis:
CALCULATED: C, 46.32; H, 3.72; N, 2.35;
FOUND: C, 48.34; H, 3.98; N, 2.40.

EXAMPLE 22

(2-Ethoxy)ethyl-N-[(propargylthio)carbonyl]-N-[dichlorophosphinylmethyl]glycinate (10.5 g.; 0.028 mol.) was dissolved in 50 ml. of diethyl ether and 50 ml. of methylene chloride. To the solution was added a solution of morpholine (9.7 g.; 0.11 mol.) in 100 ml. of diethyl ether. The resulting mixture was stirred for 16 hours at 25° C., then filtered. The filtrate was washed with 3% ammonium hydroxide, brine, 5% hydrochloric acid and again with brine. The ether layer was separated, dried and concentrated in vacuo. The residue was purified using a silica gel column with acetonitrile as the eluent to yield (2-ethoxy)ethyl-N-[(propargylthio)carbonyl]-N-[bis(morpholino)phosphinylmethyl]glycinate, dihydrate as an oil ($n_D^{25} = 1.5200$) having the following analysis:
CALCULATED: C, 44.40; H, 7.01; N, 8.17;
FOUND: C, 44.34; H, 6.53; N, 6.96.

EXAMPLE 23

To a solution of ethyl-N-[(benzylthio)carbonyl]-N-[bis(phenoxy)phosphinylmethyl]-glycinate (1.0 g.; 0.002 mol.) dissolved in 10 ml. of methylene chloride at 0° C. was slowly added a solution of metachloroperbenzoic acid (0.4 g.; B 0.002 mol.) dissolved in 100 ml. of methylene chloride. The reaction mixture was stirred for one hour and allowed to gradually warm to 25° C. The mixture was washed with 5% sodium hydroxide, dried, then concentrated in vacuo. The resulting oil was extracted into hot petroleum ether and allowed to crystallize for 16 hours to yield ethyl-N-[(benzylsulfinyl)carbonyl]-N-[bis-(phenoxy)phosphinylmethyl]-glycinate as a solid having a melting point of 106°–115° C. and the folloing analysis:
CALCULATED: C, 58.25; H, 5.08; N, 2.72; P, 6.01;
FOUND: C, 58.50; H, 5.13; L N, 2.59; P, 5.84.

EXAMPLE 24

To a solution of ethyl-N-[(benzylthio)carbonyl]-N-[bis(4-chlorophenoxy)phosphinylmethyl]-glycinate (3 g.; 0.0053 mol.) dissolved in 25 ml. of methylene chloride at 0° C. was added metachloroperbenzoic acid (1.1 g.; 0.0053 mol.). The reaction mixture was stirred for one hour at 0° C. The mixture was washed with 5% sodium hydroxide, dried and concentrated in vacuo to yield ethyl-N-[(benzylsulfinyl)carbonyl]-N-[bis(4-chlorophenoxy)phosphinylmethyl]-glycinate as a solid having a melting point of 121°–125° C. and the following analysis:
CALCULATED: C, 51.83; H, 4.14; N, 2.40;
FOUND: C, 51.54; H, 4.14; N, 2.33.

EXAMPLE 25

To a solution of ethyl-N-[(benzylthio)carbonyl]-N-[bis(3-chlorophenoxy)phosphinylmethyl]-glycinate (1.7 g.; 0.003 mol.) dissolved in 25 ml. of methylene chloride at 0° C. was added metachloroperbenzoic acid (0.6 g.; 0.003 mol.). The reaction mixture was filtered, and the filtrate was washed with 5% sodium hydroxide, dried, and concentrated in vacuo to yield ethyl-N-[(benzylsulfinyl)carbonyl]-N-[bis(3-chlorophenyl)phosphinylmethyl]-glycinate as a solid having a melting point of 68°–77° C. and the following analysis:
CALCULATED: C, 51.38; H, 4.14; N, 2.40;
FOUND: C, 51.41; H, 4.17; N, 2.40.

EXAMPLE 26

To a solution of ethyl-N-[(benzylthio)carbonyl]-N-[bis(3-methylphenoxy)phosphinylmethyl]-glycinate (2.6 g.; 0.005 mol.) dissolved in 25 ml. of methylene chloride at 0° C. was added metachloroperbenzoic acid (1.02 g.; 0.005 mol.). The reaction mixture was stirred at 0° C. for 5.25 hours, filtered and the filtrate was washed with 5% sodium hydroxide, dried, and concentrated in vacuo. To remove any remaining solvent, the residue was concentrated at 25° C. and 0.05 mm. and yielded ethyl-N-[(benzylsulfinyl)carbonyl]-N-[bis(3-methylphenoxy)phosphinylmethyl]-glycinate as an oil ($n_D^{25} = 1.5584$) having the following analysis:
CALCULATED: C, 59.66; H, 5.56; N, 2.58;
FOUND: C, 59.62; H, 5.56; N, 2.60.

EXAMPLE 27

To a solution of ethyl-N-[(benzylthio)carbonyl]-N-[bis(3-nitrophenoxy)phosphinylmethyl]-glycinate (2.0 g.; 0.0034 mol.) dissolved in 50 ml. of methylene chloride was added metachloroperbenzoic acid (0.69 g.; 0.0034 mol.) at 0° C. The reaction mixture was stirred for 4 hours while allowed to gradually warm to 25° C., then filtered. The filtrate was washed with 5% sodium hydroxide, dried, and concentrated in vacuo to yield ethyl-N-[(benzylsulfinyl)carbonyl]-N-[bis(3-nitrophenoxy)phosphinylmethyl]-glycinate (1.3 g.) as an oil ($n_D^{25}=1.5654$) having the following analysis:
CALCULATED: C, 49.59; H, 4.00; N, 6.94; FOUND: C, 49.83; H, 3.97; N, 6.82.

EXAMPLE 28

To a solution of ethyl-N-[(benzylthio)carbonyl]-N-[bis(4-methoxyphenoxy)phosphinylmethyl]-glycinate (3.0 g.; 0.0055 mol.) dissolved in 25 ml. of methylene chloride was added metachloroperbenzoic acid (1.1 g.; 0.0055 mol.) at 0° C. The reaction mixture was stirred for one hour while allowed to gradually warm to 25° C., then filtered. The filtrate was washed with 5% sodium hydroxide, dried, and concentrated in vacuo. To remove any remaining traces of solvent, the residue was concentrated at 25° C. and 0.05 mm. to yield ethyl-N-[(benzylsulfinyl)carbonyl]-N-[bis(4-methoxyphenoxy)phosphinylmethyl]-glycine as an oil ($n_D^{25}=1.5534$) having the following analysis:
CALCULATED: C, 56.34; H, 5.25; N, 2.43; FOUND: C, 56.42; H, 5.30; N, 2.40.

EXAMPLE 29

To a solution of ethyl-N-[(benzylthio)carbonyl]-N-[bis(phenoxy)phosphinylmethyl]-glycinate (2.0 g.; 0.004 mol.) dissolved in 20 ml. of 2% aqueous dioxane was added metachloroperbenzoic acid (1.72 g.; 0.010 mol.). The reaction mixture was stirred for 3 hours at 25° C. and concentrated in vacuo. The residue was taken up in benzene and the organic layer was concentrated in vacuo. The residue was dissolved in 100 ml. of a 1:1 mixture of methylene chloride:diethyl ether and the organic layer was washed with 5% sodium hydroxide, dried, and concentrated in vacuo to yield ethyl-N-[(benzylsulfonyl)carbonyl]-N-[bis(phenoxy)phosphinylmethyl]-glycinate as a solid having a melting point of 106°–110° C. and the following analysis:
CALCULATED: N, 2.64; P, 5.83; S, 6.03; FOUND: N, 2.62; P, 5.76; S, 5.89.

EXAMPLE 30

To a solution of ethyl-N-[(benzylthio)carbonyl]-N-[bis(3-chlorophenoxy)phosphinylmethyl]-glycinate (1.7 g.; 0.003 mol.) dissolved in 25 ml. of methylene chloride was added metachloroperbenzoic acid (1.5 g.; 0.0075 mol.) over a 10 minute interval. The reaction was stirred for 3 hours at 25° C. and filtered. The filtrate was washed, dried, then concentrated in vacuo. To remove any remaining solvent, the residue was concentrated at 25° C. and 0.05 mm. and yielded ethyl-N-[(benzylsulfonyl)carbonyl]-N-[bis(3-chlorophenoxy)phosphinylmethyl]glycinate (1.3 g.) as an oil ($n_D^{25}=1.5712$) having the following analysis:
CALCULATED: C, 50.01; H, 4.03; N, 2.33; FOUND: C, 50.28; H, 4.11; N, 2.41.

EXAMPLE 31

To a solution of ethyl-N-[(benzylthio)carbonyl]-N-[bis(3-methylphenoxy)phosphinylmethyl]-glycinate (2.6 g.; 0.005 mol.) dissolved in 25 ml. of methylene chloride at 25° C. was added metachloroperbenzoic acid (2.54 g.; 0.0125 mol.). The reaction mixture was stirred for 5 hours, then filtered. The filtrate was washed with 5% sodium hydroxide, dried over magnesium sulfate and concentrated in vacuo. To remove any remaining solvent, the residue was concentrated at 25° C. and 0.05 mm. and yielded ethyl-N-[(benzylsulfonyl)carbonyl]-N-[bis(3-methylphenoxy)phosphinylmethyl]-glycinate as a solid having a melting point of 47.5°–51° C. and the following analysis:
CALCULATED: C, 57.95; H, 5.40; N, 2.50; FOUND: C, 58.02; H, 5.43; N, 2.57.

EXAMPLE 32

To a solution of ethyl-N-[(benzylthio)carbonyl]-N-[bis(3-nitrophenoxy)phosphinylmethyl]-glycinate (2.0 g.; 0.0034 mol.) dissolved in 25 ml. of methylene chloride was added metachloroperbenzoic acid (1.73 g.; 0.0085 mol.) at 25° C. The reaction mixture was stirred for 3 hours and filtered. The filtrate was washed with 5% sodium hydroxide, separated with diethyl ether, dried over magnesium sulfate and concentrated in vacuo. To remove any remaining traces of solvent, the residue was concentated at 25° C. and 0.05 mm. to yield ethyl-N-[(benzylsulfonyl)carbonyl]-N-[bis(3-nitrophenoxy)phosphinylmethyl]-glycinate as an oil ($n_D^{25}=1.5732$) having the following analysis:
CALCULATED: C, 48.31; H, 3.89; N, 6.76; FOUND: C, 48.47; H, 3.89; N, 6.72.

EXAMPLE 33

To a solution of ethyl-N-[(benzylthio)carbonyl]-N-[bis(4-methoxyphenoxy)phosphinylmethyl]-glycinate (3.0 g.; 0.0055 mol.) dissolved in 25 ml. of methylene chloride was added metachloroperbenzoic acid (2.75 g.; 0.01375 mol.) at 25° C. The reaction mixture was stirred for 3 hours, then filtered. The filtrate was washed, dried, and concentrated in vacuo. To remove any remaining solvent, the residue was concentrated at 25° C. and 0.05 mm. for 16 hours and yielded ethyl-N-[(benzylsulfonyl)carbonyl]-N-[bis(4-methoxyphenoxy)phospinylmethyl]-glycinate hydrate (1.7 g.) as an oil ($n_D^{25}=1.5273$) having the following analysis:
CALCULATED: C, 53.20; H, 5.25; N, 2.29; FOUND: C, 53.42; H, 5.04; N, 2.23.

EXAMPLE 34

To a solution of ethyl-N-[(benzylthio)carbonyl]-N-[bis(4-chlorophenoxy)phosphinylmethyl]-glycinate (3 g.; 0.0055 mol.) dissolved in 25 ml. of methylene chloride was added to metachloroperbenzoic acid (2.75 g.; 0.0133 mol.) at 25° C. The reaction mixture was stirred for 3 hours and filtered. The filtrate was washed with 5% sodium hydroxide, dried, then concentrated in vacuo to yield ethyl-N-[(benzylsulfonyl)carbonyl]-N-[bis(4-chlorophenoxy)phosphinylmethyl]-glycinate as a solid having a melting point of 30°–32° C. and the following analysis:
CALCULATED: C, 50.01; H, 4.03; N, 2.33; FOUND: C, 49.89; H, 4.04; N, 2.26.

EXAMPLE 35

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
|---|---|
| 0-24% control | 0 |
| 25-49% control | 1 |
| 50-74% control | 2 |
| 75-99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg h | A | B | C | D | E | F | G | H | I | J | K |
|---|---|---|---|---|---|---|---|---|---|---|---|---|---|
| 1 | 4 | 11.2 | 1 | 1 | 1 | 1 | 4 | 4 | 2 | 2 | 1 | 2 | 3 |
| | 4 | 5.6 | 1 | 1 | 0 | 1 | 3 | 3 | 1 | 1 | 1 | 1 | 3 |
| 2* | 4 | 11.2 | 0 | 0 | 1 | 1 | 1 | 1 | 0 | 0 | 0 | 0 | 1 |
| | 4 | 5.6 | 0 | 1 | 1 | 1 | 1 | 1 | 1 | 0 | 1 | 0 | 2 |
| 3 | 2 | 11.2 | 0 | 0 | 0 | 1 | 0 | 0 | 0 | 0 | 1 | 0 | 1 |
| 4 | 4 | 11.2 | — | 3 | 4 | 1 | 4 | 4 | 2 | 2 | 1 | 3 | 3 |
| | 4 | 5.6 | 2 | 1 | 4 | 1 | 4 | 2 | 1 | 1 | 1 | 2 | 3 |
| 5 | 4 | 11.2 | 1 | 2 | 4 | 2 | 2 | 2 | 1 | 1 | 4 | 2 | 3 |
| | 4 | 5.6 | 1 | 2 | 4 | 2 | 2 | 2 | 1 | 1 | 4 | 2 | 3 |
| 6 | 4 | 11.2 | 1 | 1 | 2 | 2 | 3 | 1 | 1 | 0 | 0 | 0 | 3 |
| | 4 | 5.6 | 0 | 1 | 1 | 1 | 4 | 0 | 0 | 1 | 2 | 0 | 2 |
| 7 | 4 | 11.2 | 0 | 0 | 1 | 1 | 1 | 1 | 0 | 0 | 1 | 0 | 0 |
| | 4 | 5.6 | 0 | 0 | 1 | 1 | 1 | 0 | 0 | 0 | 1 | 0 | 1 |
| 8 | 2 | 11.2 | 0 | 1 | 0 | 0 | 0 | 0 | 0 | 0 | 0 | 0 | 0 |
| 9 | 4 | 11.2 | 0 | 0 | 0 | 1 | 0 | 1 | 0 | 1 | 0 | 0 | 1 |
| 10 | 4 | 56.0 | 0 | 1 | 0 | 1 | 1 | 0 | 1 | 0 | 0 | 0 | 1 |
| 11 | 4 | 11.2 | 1 | 0 | 1 | 1 | 2 | 1 | 0 | 0 | 0 | 0 | 3 |
| 12 | 4 | 11.2 | 1 | 2 | 4 | 2 | 4 | 4 | 0 | 2 | 1 | 1 | 2 |
| | 4 | 5.6 | 2 | 1 | 4 | 2 | 2 | 0 | 0 | 1 | 2 | 1 | 3 |
| 13 | 4 | 11.2 | 1 | 2 | 4 | 2 | 4 | 2 | 3 | 2 | 3 | 1 | 3 |
| | 4 | 5.6 | 0 | 1 | 4 | 1 | 4 | 1 | 0 | 0 | 1 | 2 | 3 |
| 14 | 4 | 11.2 | 0 | 1 | 0 | 0 | 0 | 1 | 0 | 0 | 0 | 0 | 3 |
| 15 | 4 | 11.2 | 0 | 0 | 0 | 1 | 4 | 0 | 0 | 0 | 0 | 0 | 2 |
| | 4 | 5.6 | 0 | 0 | 0 | 1 | 4 | 0 | 0 | 0 | 0 | 0 | 1 |
| 16 | 4 | 11.2 | 1 | 1 | 3 | 2 | 3 | 2 | 1 | 2 | 1 | 2 | 4 |
| | 4 | 5.6 | 0 | 0 | 3 | 1 | 2 | 1 | 1 | 1 | 1 | 1 | 3 |
| 17 | 4 | 11.2 | 0 | 0 | 0 | 0 | 0 | 0 | 0 | 0 | 0 | 0 | 1 |
| 18 | 4 | 11.2 | 0 | 0 | 0 | 1 | 0 | 0 | 0 | 0 | 1 | 0 | 2 |
| 19 | 2 | 11.2 | 0 | 0 | 0 | 1 | 0 | 0 | 0 | 0 | 0 | 0 | 1 |
| 20 | 4 | 11.2 | 0 | 0 | 1 | 1 | 2 | 0 | 2 | 1 | 2 | 2 | 2 |
| 21 | 4 | 11.2 | 0 | 0 | 0 | 1 | 0 | 0 | 0 | 1 | 1 | 0 | 3 |
| | 4 | 5.6 | 0 | 0 | 0 | 1 | 0 | 1 | 0 | 1 | 1 | 0 | 2 |
| 22 | 4 | 11.2 | 2 | 2 | 0 | — | 0 | 3 | 1 | 1 | 2 | 2 | 3 |
| | 4 | 5.6 | 0 | 0 | 0 | 1 | 0 | 0 | 0 | 0 | 0 | 0 | 0 |
| 23 | 4 | 11.2 | 2 | 3 | 3 | 2 | 3 | 3 | 3 | 2 | 1 | 3 | 3 |
| | 4 | 5.6 | 1 | 2 | 2 | 1 | 2 | 1 | 2 | 2 | 1 | 1 | 3 |
| 24 | 4 | 11.2 | 1 | 1 | 0 | 1 | 4 | 1 | 1 | 1 | 1 | 2 | 2 |
| | 4 | 5.6 | 0 | 1 | 1 | 1 | — | 0 | 2 | 2 | 0 | 1 | 3 |
| 25 | 4 | 11.2 | 3 | 3 | 3 | 3 | 4 | 4 | 2 | 2 | 2 | 3 | 4 |
| | 4 | 5.6 | 1 | 3 | 2 | 3 | 2 | 4 | 1 | 2 | 2 | 1 | 4 |
| 26 | 4 | 11.2 | 1 | 4 | 1 | 3 | 1 | 1 | 3 | 2 | 1 | 0 | 3 |
| | 4 | 5.6 | 1 | 3 | 1 | 2 | 1 | 3 | 1 | 2 | 0 | 1 | 3 |
| 27 | 4 | 11.2 | 1 | 2 | 1 | 2 | 1 | 1 | 1 | 0 | 2 | 2 | 3 |
| | 4 | 5.6 | 2 | 2 | 2 | 2 | 1 | 1 | 3 | 0 | 1 | 3 | 3 |
| 28 | 4 | 11.2 | 2 | 2 | 3 | 2 | 0 | 1 | 2 | 2 | 2 | — | 2 |
| | 4 | 5.6 | 1 | 1 | 0 | 1 | 4 | 0 | 2 | 0 | 1 | 0 | 2 |
| 29 | 4 | 11.2 | 4 | 4 | 4 | 4 | 4 | 4 | 2 | 4 | 3 | 3 | 4 |
| | 4 | 5.6 | 4 | 4 | 4 | 4 | 4 | 4 | 3 | 3 | 3 | 3 | 4 |

TABLE I-continued

| Compound of Example No. | WAT | kg h | A | B | C | D | E | F | G | H | I | J | K |
|---|---|---|---|---|---|---|---|---|---|---|---|---|---|
| 30 | 4 | 11.2 | 4 | 4 | 3 | 3 | 4 | 4 | 2 | 2 | 1 | 3 | 4 |
|  | 4 | 5.6 | 3 | 4 | 2 | 2 | 2 | 4 | 2 | 1 | 3 | 1 | 3 |
| 31 | 4 | 11.2 | 3 | 4 | 3 | 3 | 4 | 4 | 3 | 2 | 4 | 3 | 4 |
|  | 4 | 5.6 | 2 | 3 | 2 | 2 | 1 | 4 | 2 | 2 | 2 | 1 | 4 |
| 32 | 4 | 11.2 | 2 | 2 | 1 | 2 | 3 | 4 | 3 | 2 | 1 | 1 | 3 |
|  | 4 | 5.6 | 2 | 2 | 1 | 1 | 3 | 3 | 2 | 1 | 1 | 0 | 4 |
| 33 | 4 | 11.2 | 4 | 3 | 4 | 3 | 4 | 4 | 4 | 3 | 4 | 4 | 4 |
|  | 4 | 5.6 | 2 | 2 | 0 | 2 | 2 | 2 | 2 | 1 | 2 | 1 | 4 |
| 34 | 4 | 11.2 | 4 | 4 | 3 | 2 | 4 | 4 | 3 | 3 | 3 | — | 4 |
|  | 4 | 5.6 | 1 | 2 | 2 | 1 | — | 4 | 2 | 2 | 3 | — | 3 |

*Formulated immediately prior to treatment

TABLE II

| Compound of Example No. | WAT | kg h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 1 | 2 | 2 | 2 | 1 | 1 | 1 | 2 | 3 | 3 | 3 | 1 | 1 | 4 | 3 | 3 |
|  | 4 | 1.12 | 0 | 0 | 1 | 0 | 0 | 0 | 0 | 1 | 1 | 1 | 1 | 0 | 0 | 1 | 0 | 2 |
| 2* | 4 | 5.6 | 1 | 1 | 0 | 0 | 0 | 1 | 0 | 1 | 1 | 3 | 3 | 1 | 0 | 4 | 3 | 3 |
|  | 4 | 1.12 | 1 | 0 | 0 | 0 | 1 | 0 | 0 | 0 | 1 | 0 | 0 | 0 | 1 | 0 | 1 |
| 4 | 4 | 5.6 | 1 | 3 | 3 | 1 | 2 | 1 | 1 | 1 | 1 | 3 | 3 | 4 | 0 | 3 | 3 | 3 |
|  | 4 | 1.12 | 1 | 1 | 1 | 0 | 1 | 1 | 0 | 0 | 0 | 3 | 1 | 3 | 0 | 1 | 2 | 3 |
| 5 | 4 | 5.6 | 1 | 1 | 3 | 1 | 4 | 2 | 3 | 2 | 1 | 1 | 1 | 3 | 4 | 3 | 3 | 3 |
|  | 4 | 1.12 | 0 | 1 | 1 | 0 | 3 | 0 | 1 | 0 | 0 | 0 | 0 | 1 | 3 | 1 | 3 |
| 6 | 4 | 5.6 | 1 | 3 | 2 | 1 | 3 | 1 | 2 | 2 | 1 | 3 | 3 | 3 | 1 | 4 | 3 | 4 |
|  | 4 | 1.12 | 0 | 2 | 0 | 0 | 2 | 0 | — | 1 | 0 | 4 | 2 | 2 | 3 | 2 | 2 | 3 |
| 11 | 4 | 5.6 | 1 | 3 | 2 | 2 | 3 | 2 | 2 | 2 | 1 | 2 | 3 | 1 | 3 | 4 | 3 | 4 |
|  | 4 | 1.12 | 0 | 0 | 1 | 1 | 0 | 1 | 0 | 1 | 0 | 1 | 1 | 1 | 1 | 2 | 3 | 2 |
| 12 | 4 | 5.6 | 1 | 4 | 4 | 2 | 3 | 1 | 4 | 2 | 2 | 4 | 3 | 4 | 0 | 3 | 3 | 3 |
|  | 4 | 1.12 | 0 | 1 | 1 | 0 | 1 | 0 | 0 | 1 | 0 | 1 | 0 | 3 | 0 | 2 | 1 | 2 |
|  | 4 | 0.28 | 0 | 1 | 1 | 0 | 0 | 0 | 0 | 1 | 0 | 0 | 0 | 2 | 0 | 0 | 1 | 3 |
| 13 | 4 | 5.6 | 0 | 2 | 2 | 1 | 3 | 2 | 2 | 2 | 1 | 4 | 1 | 3 | 2 | 3 | 3 | 3 |
|  | 4 | 1.12 | 1 | 1 | 0 | 0 | 2 | 0 | 1 | 1 | 0 | 1 | 1 | 2 | 0 | 2 | 2 | 2 |
| 14 | 4 | 5.6 | 0 | 0 | 0 | 0 | 0 | 1 | 0 | 1 | 2 | 0 | 0 | 0 | 0 | 2 | 1 | 3 |
| 16 | 4 | 5.6 | 1 | 4 | 3 | 3 | 3 | 1 | 1 | 2 | 2 | 4 | 3 | 4 | 3 | 4 | 4 | 4 |
|  | 4 | 1.12 | 1 | 1 | 2 | 2 | 2 | 1 | 1 | 1 | 2 | 2 | 1 | 1 | 1 | 2 | 3 | 3 |
|  | 4 | 0.28 | 1 | 0 | 0 | 0 | 1 | 1 | 0 | 1 | 1 | 1 | 1 | 1 | 1 | 3 | 2 | 3 |
| 21 | 4 | 5.6 | 0 | 2 | 2 | 0 | 2 | — | 4 | — | 1 | 2 | 2 | 1 | 1 | 3 | 3 | 3 |
|  | 2 | 1.12 | 0 | 0 | 0 | 0 | 0 | 0 | 0 | — | 0 | 0 | 0 | 0 | 0 | 1 | 1 | 3 |
| 22 | 2 | 5.6 | 0 | 0 | 1 | 1 | 1 | — | 1 | — | 0 | 2 | 2 | 1 | 1 | 2 | 2 | 3 |
|  | 2 | 1.12 | 0 | 0 | 0 | 0 | 0 | — | 0 | — | 0 | 0 | 0 | 0 | 0 | 1 | 0 | 1 |
| 23 | 4 | 5.6 | 2 | 2 | 2 | 2 | 2 | 3 | 2 | 2 | 4 | 2 | 3 | 2 | 1 | 4 | 3 | 3 |
|  | 4 | 1.12 | 1 | 1 | 1 | 0 | 2 | 1 | 1 | 2 | 2 | 1 | 2 | 1 | 1 | 3 | 3 | 3 |
|  | 4 | 0.28 | 1 | 0 | 0 | 0 | 1 | 1 | 1 | 1 | 1 | 1 | 3 | 0 | 0 | 3 | 2 | 2 |
| 24 | 4 | 5.6 | 1 | 4 | 2 | 2 | 4 | 4 | 2 | 2 | 2 | 4 | 3 | 3 | 3 | 3 | 3 | 4 |
|  | 4 | 1.12 | 1 | 1 | 1 | 1 | 2 | 2 | 1 | 2 | 1 | 0 | 1 | 1 | 0 | 3 | 2 | 3 |
| 25 | 4 | 5.6 | 3 | 3 | 2 | 2 | 3 | 3 | 2 | 1 | 1 | 1 | 3 | 1 | 2 | 4 | 2 | 3 |
|  | 4 | 1.12 | 1 | 4 | 0 | 0 | 2 | 2 | 0 | 1 | 4 | 3 | 3 | 0 | 2 | 3 | 2 | 2 |
| 26 | 4 | 5.6 | 2 | 2 | 3 | 3 | 3 | 3 | 1 | 2 | 4 | 2 | 2 | 2 | 2 | 3 | 3 | 4 |
|  | 4 | 1.12 | 0 | 0 | 0 | 1 | 2 | 2 | 0 | 1 | 1 | 0 | 0 | 1 | 0 | 3 | 2 | 2 |
| 27 | 4 | 5.6 | 2 | 4 | 3 | 4 | 3 | 3 | 2 | 3 | 4 | 4 | 4 | 2 | 3 | 3 | 3 | 4 |
|  | 4 | 1.12 | 1 | 1 | 1 | 1 | 3 | 2 | 1 | 2 | 0 | 4 | 2 | 0 | 1 | 4 | 3 | 3 |
|  | 4 | 0.28 | 0 | 0 | 1 | 0 | 1 | 1 | 0 | 1 | 0 | 0 | 0 | 0 | 1 | 1 | 1 | 2 |
| 28 | 4 | 5.6 | 2 | 1 | 1 | 2 | 4 | 3 | 2 | 2 | 2 | 1 | 3 | 2 | 2 | 4 | 4 | 3 |
|  | 4 | 1.12 | 1 | 0 | 1 | 0 | 1 | 2 | 0 | 1 | 0 | 0 | 1 | 1 | 1 | 2 | 2 | 3 |
| 29 | 4 | 5.6 | 1 | 2 | 2 | 1 | 2 | 2 | 4 | 2 | 3 | 2 | 3 | 3 | 0 | 3 | 3 | 3 |
|  | 4 | 1.12 | 1 | 1 | 2 | 2 | 2 | 1 | 1 | 2 | 2 | 2 | 3 | 2 | 1 | 3 | 3 | 3 |
|  | 4 | 0.28 | 1 | 1 | 1 | 1 | 1 | 1 | 0 | 1 | 2 | 1 | 1 | 1 | 0 | 1 | 1 | 2 |
|  | 4 | 5.6 | 3 | 4 | 4 | 4 | 4 | 3 | 3 | 3 | 4 | 4 | 4 | 4 | 3 | 4 | 4 | 4 |
|  | 4 | 1.12 | 2 | 2 | 2 | 1 | 2 | 2 | 1 | 1 | 4 | 4 | 3 | 2 | 1 | 3 | 3 | 3 |
|  | 4 | 0.28 | 1 | 0 | 1 | 1 | 1 | 1 | 0 | 1 | 0 | 1 | 0 | 1 | 0 | 3 | 2 | 3 |
| 30 | 4 | 5.6 | 3 | 4 | 4 | 3 | 3 | 4 | 3 | 3 | 4 | 3 | 4 | 3 | 4 | 3 | 4 |
|  | 4 | 1.12 | 0 | 2 | 1 | 1 | 1 | 1 | 2 | 1 | 0 | 0 | 1 | 0 | 0 | 3 | 1 | 2 |
| 31 | 4 | 5.6 | 4 | 4 | 4 | 4 | 4 | 4 | 3 | 3 | 4 | 4 | 4 | 4 | 4 | 4 | 4 | 4 |
|  | 4 | 1.12 | 2 | 3 | 2 | 2 | 4 | 2 | 2 | 2 | 2 | 1 | 2 | 2 | 4 | 4 | 3 | 4 |
|  | 4 | 0.28 | 0 | 1 | 0 | 1 | 1 | 2 | 0 | 2 | 1 | 1 | 1 | 1 | 2 | 2 | 3 |
| 32 | 4 | 5.6 | 2 | 3 | 2 | 1 | 4 | 2 | 2 | 2 | 1 | 2 | 4 | 2 | 3 | 4 | 3 | 3 |
|  | 4 | 1.12 | 1 | 1 | 2 | 1 | 2 | 2 | 0 | 2 | 0 | 1 | 1 | 1 | 2 | 4 | 2 | 3 |
|  | 4 | 0.28 | 0 | 0 | 0 | 0 | 0 | 0 | 0 | 1 | 0 | 0 | 0 | 0 | 1 | 1 | 2 |
| 33 | 4 | 5.6 | 3 | 4 | 4 | 3 | 4 | 3 | 3 | 4 | 3 | 4 | 4 | 3 | 4 | 4 | 4 | 4 |
|  | 4 | 1.12 | 1 | 4 | 3 | 1 | 3 | 2 | 2 | 2 | 1 | 4 | 4 | 1 | 2 | 4 | 3 | 3 |
|  | 4 | 0.28 | 0 | 0 | 1 | 0 | 2 | 2 | 2 | 2 | 4 | 1 | 1 | 0 | 1 | 2 | 2 | 3 |
| 34 | 4 | 5.6 | 3 | 4 | 3 | 3 | 3 | 3 | 2 | 3 | 4 | 4 | 3 | 3 | 4 | 4 | 4 |
|  | 4 | 1.12 | 1 | 2 | 3 | 1 | 3 | 2 | 2 | 2 | 1 | 1 | 2 | 2 | 2 | 4 | 3 | 3 |
|  | 4 | 0.28 | 1 | 1 | 0 | 0 | 0 | 2 | 1 | 2 | 0 | 1 | 1 | 0 | 2 | 2 | 2 | 3 |

*Formulated immediately prior to treatment.

EXAMPLE 36

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Tables III and IV.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the tables are identified by the same code letters used in the previous example.

TABLE III

| Compound of Example No. | WAT | kg h | A | B | C | D | E | F | G | H | I | J | K |
|---|---|---|---|---|---|---|---|---|---|---|---|---|---|
| 1 | 2 | 11.2 | 0 | 0 | 1 | 0 | 1 | 0 | 3 | 1 | 0 | 0 | 3 |
| 2* | 2 | 11.2 | 0 | 0 | 0 | 0 | 0 | 0 | 3 | 1 | 0 | 1 | 1 |
| 3 | 2 | 11.2 | 0 | 0 | 0 | 0 | 0 | 0 | 0 | 0 | 0 | 0 | 0 |
| 4 | 2 | 11.2 | 0 | 0 | 1 | 0 | 0 | 0 | 3 | 3 | 0 | 0 | 2 |
| 5 | 4 | 11.2 | 0 | 0 | 2 | 1 | 3 | 0 | 3 | 0 | 0 | 1 | 2 |
| 6 | 2 | 11.2 | 0 | 1 | 1 | 0 | 1 | 0 | 0 | 0 | 0 | 0 | 1 |
| 7 | 2 | 11.2 | 2 | 0 | 0 | 0 | 2 | 0 | 0 | 0 | 0 | 0 | 0 |
| 8 | 2 | 11.2 | 0 | 0 | 0 | 0 | 3 | 0 | 0 | 0 | 0 | 0 | 0 |
| 9 | 2 | 11.2 | 0 | 0 | 0 | 0 | 0 | 0 | 0 | 0 | 0 | 0 | 0 |
| 10 | 2 | 11.2 | 0 | 0 | 0 | 0 | 0 | 0 | 0 | 0 | 0 | 0 | 0 |
| 11 | 2 | 11.2 | 0 | 0 | 0 | 0 | 0 | 0 | 0 | 0 | 0 | 0 | 0 |
| 12 | 4 | 11.2 | 1 | 0 | 0 | 0 | 3 | 0 | 0 | 0 | 0 | 1 | 0 |
| 13 | 2 | 11.2 | 0 | 0 | 1 | 0 | 1 | 0 | 0 | 0 | 0 | 0 | 0 |
| 14 | 2 | 11.2 | 0 | 0 | 0 | 0 | 0 | 0 | 0 | 0 | 0 | 0 | 0 |
| 15 | 2 | 11.2 | 0 | 0 | 0 | 0 | 0 | 0 | 0 | 0 | 0 | 0 | 0 |
| 16 | 2 | 11.2 | 0 | 0 | 0 | 0 | 0 | 0 | 0 | 1 | 0 | 0 | 0 |
| 17 | 2 | 11.2 | 0 | 0 | 0 | 0 | 0 | 0 | 0 | 0 | 0 | 0 | 0 |
| 18 | 2 | 11.2 | 0 | 1 | 0 | 0 | 0 | 0 | 1 | 0 | 0 | 0 | 1 |
| 19 | 2 | 11.2 | 1 | 0 | 0 | 0 | 0 | 0 | 0 | 0 | 0 | 1 | 2 |
| 20 | 2 | 11.2 | 0 | 0 | 0 | 0 | 0 | 1 | 0 | 0 | 0 | 0 | 1 |
| 21 | 2 | 11.2 | 0 | 0 | 0 | 0 | 0 | 0 | 0 | 0 | 0 | 0 | 0 |
| 22 | 2 | 11.2 | 0 | 0 | 0 | 0 | 0 | 0 | 0 | 0 | 0 | 0 | 0 |
| 23 | 2 | 11.2 | 2 | 0 | 0 | 0 | 0 | 0 | 0 | 0 | 0 | 0 | 0 |
| 24 | 2 | 11.2 | 2 | 0 | 0 | 0 | 0 | 2 | 0 | 0 | 0 | 0 | 0 |
| 25 | 2 | 11.2 | 2 | 0 | 0 | 1 | 1 | 2 | 3 | 0 | 0 | 0 | 3 |
| 26 | 4 | 11.2 | 1 | 0 | 0 | 0 | 1 | 0 | 0 | 0 | 1 | 0 | 0 |
| 27 | 2 | 11.2 | 1 | 0 | 0 | 0 | 0 | 0 | 0 | 0 | 0 | 0 | 0 |
| 28 | 2 | 11.2 | 0 | 0 | 0 | 0 | 3 | 0 | 0 | 0 | 0 | 0 | 0 |
| 29 | 2 | 11.2 | 3 | 0 | 0 | 0 | 0 | 0 | 2 | 1 | 2 | 0 | 1 |
| 30 | 2 | 11.2 | 2 | 0 | 0 | 1 | 1 | 1 | 0 | 0 | 0 | 0 | 3 |
| 31 | 2 | 11.2 | 1 | 0 | 0 | 0 | 0 | 0 | 0 | 0 | 0 | 0 | 0 |
| 32 | 2 | 11.2 | 0 | 0 | 0 | 0 | 0 | 0 | 0 | 0 | 0 | 0 | 0 |
| 33 | 2 | 11.2 | 0 | 0 | 0 | 0 | 0 | 3 | 0 | 0 | 0 | 0 | 1 |
| 34 | 2 | 11.2 | 2 | 0 | 1 | 0 | 0 | 0 | 0 | 1 | 3 | 0 | 0 |

*Formulated immediately prior to treatment.

TABLE IV

| Compound of Example No. | WAT | kg h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 0 | 0 | 0 | 1 | 1 | 0 | 0 | 0 | 1 | 0 | 0 | 0 | 0 | 2 | 2 | 1 |
|   | 2 | 1.12 | 0 | 0 | 0 | 0 | 0 | 0 | 0 | 0 | 0 | 0 | 0 | 0 | 0 | 0 | 0 | 0 |
| 5 | 4 | 11.2 | 0 | 3 | 0 | 0 | 3 | 0 | 3 | 3 | 2 | 3 | 1 | 3 | 3 | 3 | 3 | 3 |
|   | 2 | 5.6 | 0 | 1 | 0 | 0 | 2 | 1 | 1 | 2 | 1 | 0 | 0 | 1 | 0 | 3 | 3 | 3 |
|   | 2 | 1.12 | 0 | 1 | 0 | 0 | 0 | 1 | 2 | 1 | 2 | — | 2 | 0 | 0 | 1 | 2 | 0 |
|   | 2 | 0.28 | 0 | — | 1 | 0 | 0 | 0 | 2 | 0 | 0 | 0 | 0 | 0 | 0 | 1 | 2 | 0 |
| 25 | 2 | 5.6 | 0 | 0 | 0 | 1 | 1 | 0 | 0 | 0 | 0 | 0 | 0 | 0 | 0 | 1 | 0 | 0 |
|   | 2 | 1.12 | 0 | 0 | 0 | 0 | 0 | 0 | 0 | 0 | 0 | 0 | 0 | 0 | 0 | 0 | 0 | 0 |
| 30 | 2 | 5.6 | 0 | 0 | 0 | 0 | 0 | 0 | 0 | 0 | 0 | 0 | 0 | 0 | 0 | 0 | 0 | 0 |
|   | 2 | 1.12 | 0 | 0 | 0 | 0 | 0 | 0 | 0 | 0 | 0 | 0 | 0 | 0 | 0 | 0 | 0 | 0 |
| 33 | 2 | 5.6 | 0 | 0 | 0 | 0 | 0 | 0 | 0 | 0 | 0 | 0 | 0 | 0 | 0 | 3 | 3 | 2 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Tables III and IV, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

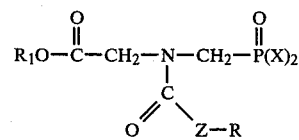

wherein R is selected from the group consisting of lower alkyl, lower alkenyl, lower alkynyl or benzyl; $R_1$ is selected from the group consisting of lower alkyl or lower alkoxyalkyl; Z is sulfinyl, and X is phenoxy or phenoxy substituted with up to three groups individually selected from the class consisting of lower alkyl, lower alkoxy, halogen and nitro.

2. A compound of claim 1 wherein $R_1$ is lower alkyl.
3. A compound of claim 2 wherein R is benzyl.
4. A compound of claim 3 which is ethyl-N-[(benzylsulfinyl)carbonyl]-N-[bis(3-chlorophenoxy)phosphinylmethyl]glycinate.
5. A herbicidal composition comprising an inert adjuvant and a herbicidally effective amount of a compound of the formula

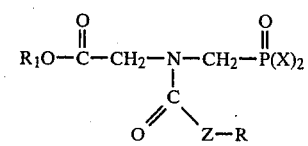

wherein R is selected from the group consisting of lower alkyl, lower alkenyl, lower alkynyl or benzyl; $R_1$ is selected from the group consisting of lower alkyl or lower alkoxyalkyl; Z is sulfinyl, and X is phenoxy or phenoxy substituted with up to three groups individually selected from the class consisting of lower alkyl, lower alkoxy, halogen and nitro.

6. A composition of claim 5 wherein $R_1$ is lower alkyl.

7. A composition of claim 6 wherein R is benzyl.

8. A composition of claim 7 which is ethyl-N-[(benzylsulfinyl)carbonyl]-N-[bis(3-chlorophenoxy)phosphinylmethyl]glycinate.

9. A method of controlling undesired plants which comprises contacting said plants or the plant growth medium with a herbicidal amount of a compound of the formula

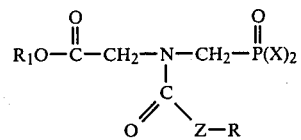

wherein R is selected from the group consisting of lower alkyl, lower alkenyl, lower alkynyl or benzyl; $R_1$ is selected from the group consisting of lower alkyl or lower alkoxyalkyl; Z is sulfinyl, and X is phenoxy or phenoxy substituted with up to three groups individually selected from the class consisting of lower alkyl, lower alkoxy, halogen and nitro.

10. A method of claim 9 wherein $R_1$ is lower alkyl.

11. A method of claim 10 wherein R is benzyl.

12. A method of claim 11 which is ethyl-N-[(benzylsulfonyl)carbonyl]-N-[bis(3-chlorophenoxy)phosphinylmethyl]glycinate.

* * * * *